(12) United States Patent
Shaban et al.

(10) Patent No.: US 8,479,562 B2
(45) Date of Patent: Jul. 9, 2013

(54) METHOD AND APPARATUS OF IDENTIFYING EXPLOSIVES AND CHEMICAL WARFARE ON-FIELD WITH CAPACITATIVE NEUTRONS GENERATOR

(76) Inventors: Yasser Ragab Shaban, Sofia (BG); Milen K. Panteleev, Concord, CA (US)

(*) Notice: Subject to any disclaimer, the term of this patent is extended or adjusted under 35 U.S.C. 154(b) by 212 days.

(21) Appl. No.: 13/026,334

(22) Filed: Feb. 14, 2011

(65) Prior Publication Data
US 2012/0205261 A1 Aug. 16, 2012

(51) Int. Cl.
*G01N 27/26* (2006.01)
*C25B 9/00* (2006.01)

(52) U.S. Cl.
USPC ........... 73/35.14; 205/793; 204/265; 204/415

(58) Field of Classification Search
USPC ........................................................ 73/35.14
See application file for complete search history.

(56) References Cited

U.S. PATENT DOCUMENTS

| | | | |
|---|---|---|---|
| 2009/0095895 A1* | 4/2009 | Dent | 250/251 |
| 2010/0090097 A1* | 4/2010 | Koltick | 250/251 |
| 2010/0208267 A1* | 8/2010 | Rogers et al. | 356/432 |

* cited by examiner

*Primary Examiner* — Hezron E Williams
*Assistant Examiner* — Gregory J Redmann

(57) ABSTRACT

The aim of the present invention is to identify stationary and moveable high explosives and chemical warfare on-field with a unique structure of a portable neutrons generator used in strategic and public places, vehicles and airplanes. The present invention includes also a unique operation of fusion fuel below breakdown which is characterized with high production efficiency. The analysis of identifying the elements and their concentrations is also introduced in the present invention.

3 Claims, 10 Drawing Sheets

Table 1

Figure 1:
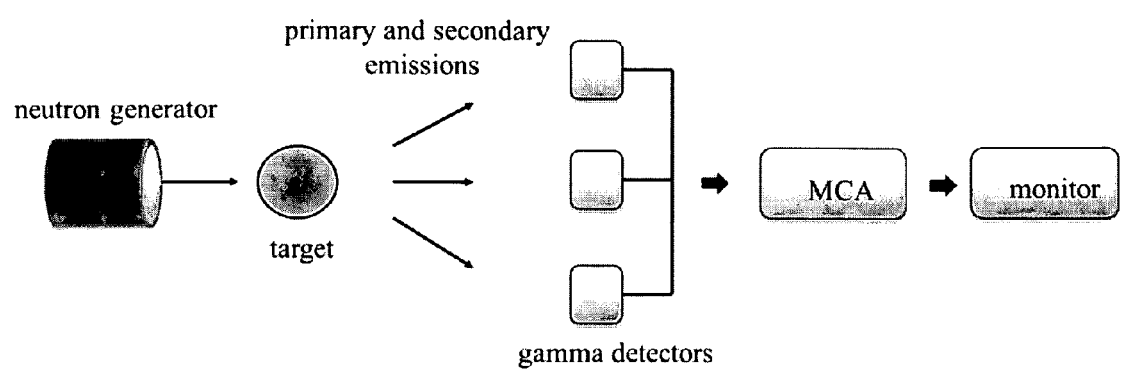

| neutron energy, E eV | ln (E₀/E) | NEG layer thickness mm ± 1 mm |
|---|---|---|
| 1 | 13.8 | 50 |
| 10 | 11.5 | 42 |
| 100 | 9.2 | 33 |
| 1000 = K | 6.9 | 25 |
| 10 K | 4.6 | 16 |
| 100 K | 2.3 | 8 |
| 1000 K | 0 | void |

FIG. 6

| neutron energy, E eV | ln (E₀/E) | NEG layer thickness mm ± 1 mm |
|---|---|---|
| 1 | 13.8 | 50 |
| 10 | 11.5 | 42 |
| 100 | 9.2 | 33 |
| 1000 = K | 6.9 | 25 |
| 10 K | 4.6 | 16 |
| 100 K | 2.3 | 8 |
| 1000 K | 0 | void |

FIG. 7

| nuclear reaction | energy of emitted γ, keV | γ emission probability (%) | half-life of product isotope | natural abundance of reactant isotope |
|---|---|---|---|---|
| $Al^{27}(n,p)Mg^{27}$ | 843, 1014 | 71.8, 28.2 | 9.45 m | 100 |
| $Al^{27}(n,\alpha)Na^{24}$ | 1368 | 100 | 15 h | 100 |
| $Fe^{58}(n,\gamma)Fe^{59}$ | 1098.6, 1291.5 | 54, 43 | 45 d | 0.31 |
| $Fe^{54}(n,p)Mn^{54}$ | 834.8 | 100 | 291 d | 5.84 |
| $Fe^{56}(n,p)Mn^{56}$ | 846, 1811 | 78.4, 21.6 | 2.58 h | 91.68 |
| $Si^{30}(n,\gamma)Si^{31}$ | 1266.2 | 100 | 2.62 h | 3.05 |
| $Si^{29}(n,p)Al^{29}$ | 1273.3 | 93 | 6.6 m | 4.98 |
| $S^{36}(n,\gamma)S^{37}$ | 3102.4 | 100 | 5 m | 0.017 |
| $S^{34}(n,\alpha)Si^{31}$ | 1266.2 | 100 | 2.62 h | 4.2 |
| $Ge^{76}(n,\gamma)Ge^{77}$ | 211, 215 | 27.2, 27.2 | 11.3 h | 7.67 |
| $Ge^{76}(n,\gamma)Ge^{77m}$ | 215 | 27.2 | 54 s | 7.67 |
| $Ge^{74}(n,\gamma)Ge^{75}$ | 264 | 86 | 82 m | 36.7 |
| $Ge^{74}(n,\gamma)Ge^{75m}$ | 139.8 | 100 | 49 s | 36.7 |
| $P^{31}(n,p)Si^{31}$ | 1266 | 100 | 2.62 h | 100 |
| $F^{19}(n,\gamma)F^{20}$ | 1633 | 100 | 11 s | 100 |
| $As^{75}(n,\gamma)As^{76}$ | 559 | 80.6 | 26.5 h | 100 |
| $Ca^{46}(n,\gamma)Ca^{47}$ | 159.8, 1296.9 | 50.5, 45.4 | 3.43 d, 4.5 d | 0.0033 |
| $Ca^{48}(n,\gamma)Ca^{49}$ | 3084 | 90.9 | 8.72 m | 0.185 |
| $Cl^{37}(n,\gamma)Cl^{38}$ | 1642, 2166 | 58.8, 41.2 | 37.2 m | 24.6 |
| $B^{10}(n,\gamma)B^{11}$ | 477.7 | 100 | n.a | 80 |
| $O^{18}(n,\gamma)O^{19}$ | 197 | 100 | 29 s | 0.204 |
| $N^{15}(n,\gamma)N^{16}$ | 6129, 7115 | 50, 50 | 7.13 s | 0.37 |
| $H^{1}(n,\gamma)H^{2}$ | 2223.3 | 100 | n.a | 99.985 |
| $C^{12}(n,p)N^{12}$ | 4439 | 100 | 0.011 s | 98.9 | s stands for seconds, m for minutes, h for hours and d for days.

FIG. 8

| Element | CW and HE Munitions | | | | |
|---|---|---|---|---|---|
| | TNT | Sarin (GB) | (VX) | Mustard (HD) | Lewisite |
| H | 2.2 | 7.1 | 9.7 | 5.0 | 1.0 |
| C | 37.0 | 34.3 | 49.4 | 30.2 | 11.4 |
| O | 42.3 | 22.9 | 12.0 | xxxxx | xxxxx |
| N | 18.5 | xxxxx | 5.2 | xxxxx | xxxxx |
| F | xxxxx | 13.6 | xxxxx | xxxxx | xxxxx |
| Al | xxxxx | xxxxx | xxxxx | xxxxx | xxxxx |
| P | xxxxx | 22.1 | 11.6 | xxxxx | xxxxx |
| S | xxxxx | xxxxx | 12.0 | 20.1 | xxxxx |
| Cl | xxxxx | xxxxx | xxxxx | 44.7 | 51.3 |
| As | xxxxx | xxxxx | xxxxx | xxxxx | 36.1 |

FIG. 9

| Target (Fill) | Containers | Key Elements |
|---|---|---|
| | | Secondary Elements |
| HD | ton container | Cl, S |
| | | C, H |
| VX | land mines | P, S |
| | | O, N |
| VX | 155 mm shell | P, S |
| | | O, N |
| GB | weteye bomb | P, F |
| | | O |
| GB | ton container | P, F |
| | | O |
| GB | 155 mm shell | P, F |
| | | O |
| TNT | 8 inch shell | Free of : P, F, S and Cl |
| | | H, C, O, N |
| Comp. B | 155 mm shell | Free of : P, F, S and Cl |
| | | H, C, O, N |

FIG. 10

| neutron energy, eV | nuclear reaction | energy of emitted $\gamma$, keV | $\gamma$ emission probability (%) | $(\sigma \varphi)_c$ reactions/sec |
|---|---|---|---|---|
| 0.025 | $Lu^{175}(n,\gamma)Lu^{176m}$ | 88.3 | 100 | to be measured |
| 0.142 | $Lu^{176}(n,\gamma)Lu^{177}$ | 208.4 | 18 | ............ |

FIG. 11

| neutron energy, eV | nuclear reaction | energy of emitted γ, keV | γ emission probability (%) | $(\sigma \varphi)_c$ reactions/sec |
|---|---|---|---|---|
| 1.457 | $In^{115}(n,\gamma)In^{116m}$ | 1293.4, 1097.1 | 38.3, 26.8 | to be measured |
| 4.9 | $Au^{197}(n,\gamma)Au^{198}$ | 411.8 | 100 | .................. |
| 5.20 | $Ag^{109}(n,\gamma)Ag^{110m}$ | 657.8, 884.5 | 34.4, 25.4 | .................. |
| 6.7 | $U^{238}(n,\gamma)U^{239}$ | 74.7 | 100 | .................. |
| 18.8 | $W^{186}(n,\gamma)W^{187}$ | 685.7, 479.3 | 31.4, 26.7 | .................. |
| 24 | $Th^{232}(n,\gamma)Th^{233}$ | 86.6, 162.3, 169.3, 459.2, 491.1, 499.4, 670.0 | 14 (in all) | .................. |
| 132 | $Co^{59}(n,\gamma)Co^{60}$ | 1173.1, 1332.4 | 50, 50 | .................. |
| 230 | $Fe^{58}(n,\gamma)Fe^{59}$ | 1098.6, 1291.5 | 54, 43 | .................. |
| 337 | $Mn^{56}(n,\gamma)Mn^{57}$ * | 846.9 | 71 | .................. |
| 480 | $Mo^{98}(n,\gamma)Mo^{99}$ | 140.6 | 74 | .................. |
| 580 | $Cu^{63}(n,\gamma)Cu^{64}$ ** | 1345.5 | 100 | .................. |
| 1710 | $Na^{23}(n,\gamma)Na^{24}$ *** | 2753.6, 1368.4 | 52, 48 | .................. |
| 5000 | $Sc^{45}(n,\gamma)Sc^{46}$ **** | 889.4, 1120.3 | 50, 50 | .................. |

FIG. 12

| neutron energy, MeV | nuclear reaction | energy of emitted γ, keV | γ emission probability (%) | $(\sigma \varphi)_c$ reactions/sec |
|---|---|---|---|---|
| 0.1 | $Nb^{93}(n,2n)Nb^{92m}$ | 934.6 | 100 | to be measured |
| 0.8 | $Rh^{103}(n,2n)Rh^{102m}$ | 475.1 | 75.2 | ............... |
| 1.2 | $In^{115}(n,n')In^{115m}$ | 335 | 46.7 | ............... |
| 2.2 | $Ti^{47}(n,p)Sc^{47}$ | 159.8 | 100 | ............... |
| 2.8 | $Zn^{64}(n,p)Cu^{64}$ | 184.2, 93.2 | 58.8, 41.2 | ............... |
| 2.8 | $Ni^{58}(n,p)Co^{58}$ | 810.3 | 98.8 | ............... |
| 3.1 | $Fe^{54}(n,p)Mn^{54}$ | 834.8 | 100 | ............... |
| 3.9 | $Ti^{46}(n,p)Sc^{46}$ | 888, 1119 | 50, 50 | ............... |
| 4.4 | $Al^{27}(n,p)Mg^{27}$ | 843, 1014 | 71.8, 28.2 | ............... |
| 6.0 | $Fe^{56}(n,p)Mn^{56}$ | 846, 1811 | 78.4, 21.6 | ............... |
| 7.2 | $Al^{27}(n,\alpha)Na^{24}$ | 1368 | 100 | ............... |
| 7.6 | $Ti^{48}(n,p)Sc^{48}$ | 982, 1037, 1311 | 33.6, 32.7, 33.6 | ............... |
| 11.0 | $Nb^{93}(n,2n)Nb^{92m}$ | 934.6 | 100 | ............... |
| 11.5 | $V^{51}(n,\alpha)Sc^{48}$ | 983.5, 1037.4 | 50.5, 49.5 | ............... |
| 13.5 | $Ni^{58}(n,2n)Ni^{57}$ | 1378.4 | 86.2 | ............... |

METHOD AND APPARATUS OF IDENTIFYING EXPLOSIVES AND CHEMICAL WARFARE ON-FIELD WITH CAPACITATIVE NEUTRONS GENERATOR

CROSS-REFERENCE TO RELATED APPLICATIONS

Not applicable

STATEMENT REGARDING FEDERALLY SPONSORED RESEARCH OR DEVELOPMENT

Individual Efforts

BACKGROUND

The application of neutrons activations to identify explosives was earlier proposed by R. Meyer and S. Budavari in 1987. Since 1987, the radioactive nuclide Cf-252 (half-life of 2.5 years) was being used to identify explosives.

The present invention includes the applications of neutron generator (non-radioactive) and an analysis of evaluations the concentrations of elements present in explosives.

BRIEF DESCRIPTION OF DRAWINGS AND TABLES

Figures and tables included in this invention are briefly described as follows.

FIG. 1 The general description of neutrons activation, gamma emission and detection.

Figure 2:
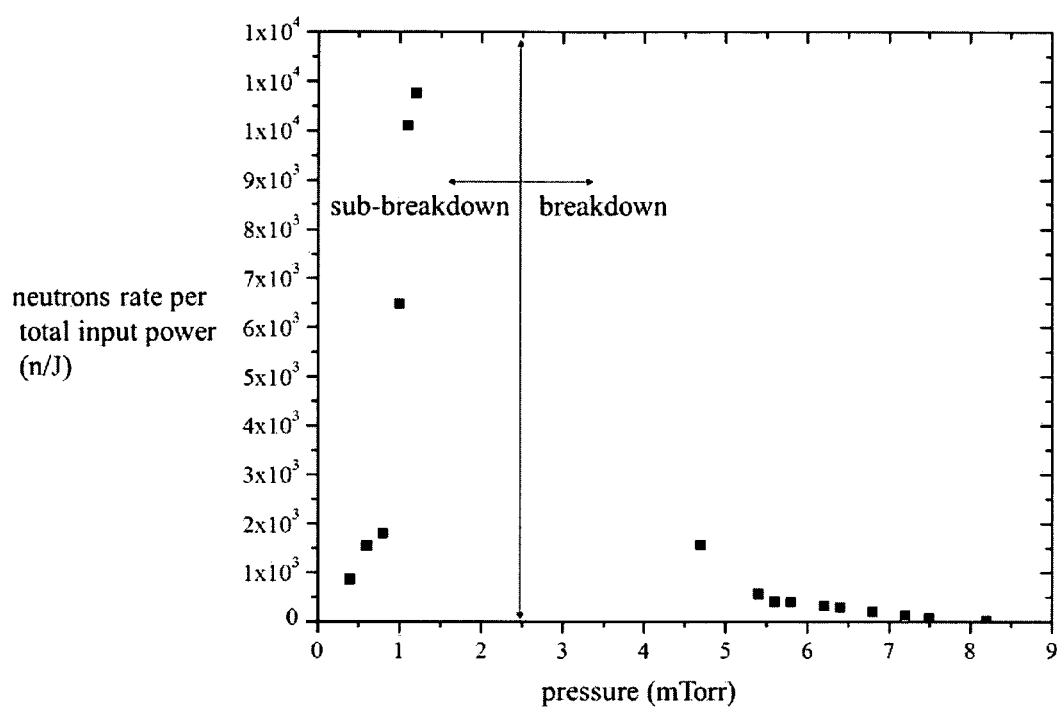

FIG. 2 Illustrations of neutrons production efficiency n/(sec-W) as a function of pressure before and after PV breakdown regime. The breakdown condition for the given data is equal to 200 kV-mTorr.

Figure 3:
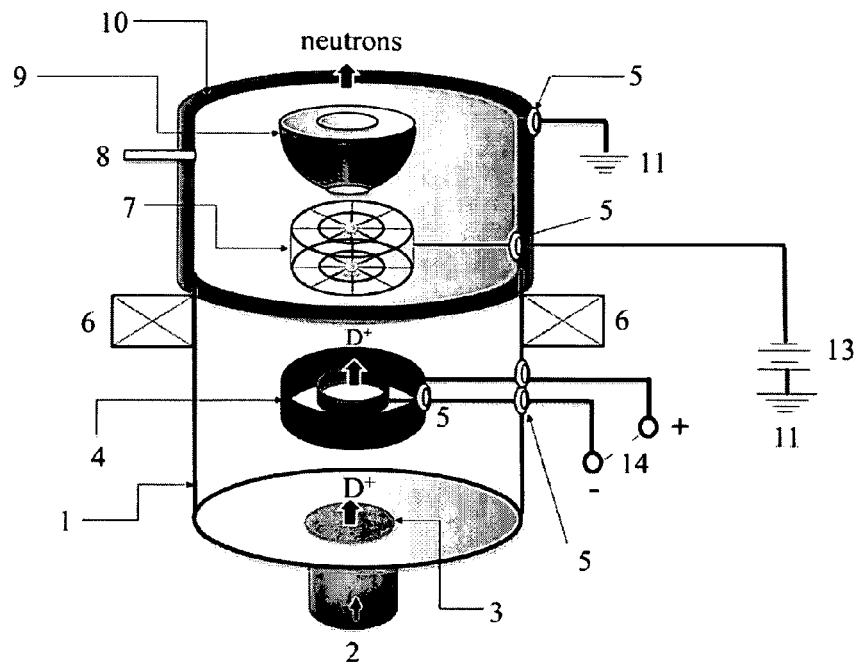

FIG. 3 Illustration of the main components of the present invention: the neutrons generator.

Figure 4:
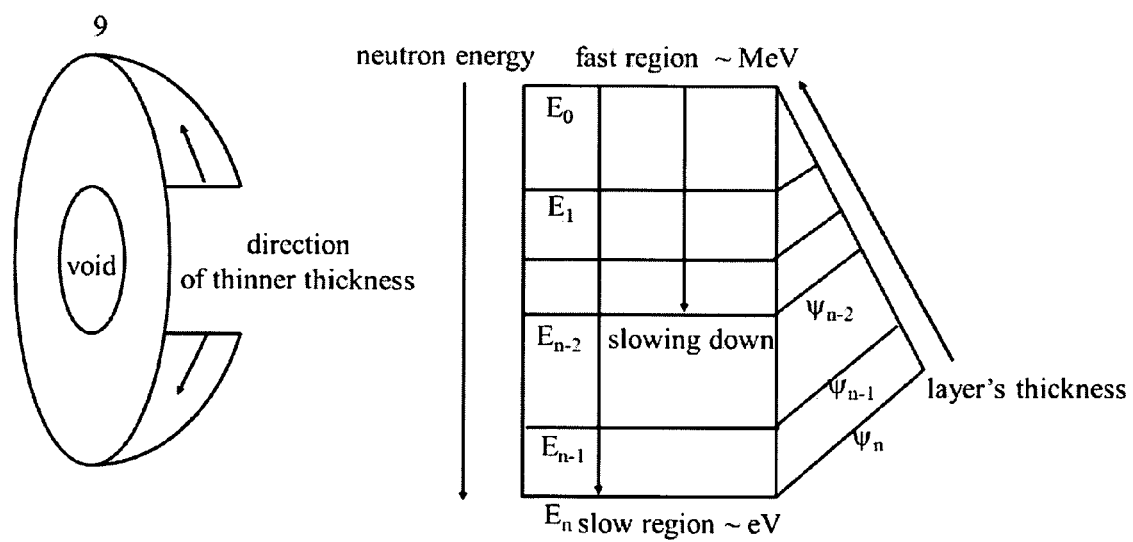

FIG. 4 The structure of the neutron energy grating NEG thermalizer which is a part of the neutrons generator.

Figure 5:
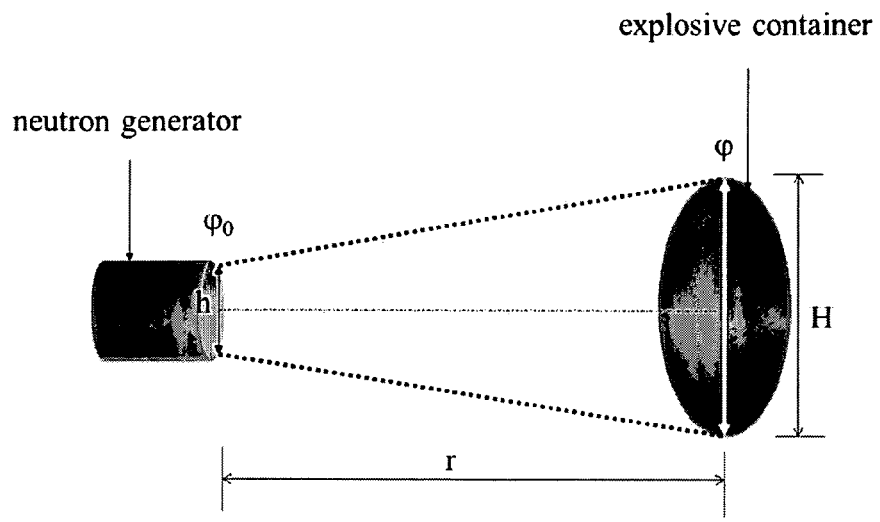

FIG. 5 The geometric of neutrons intersection with the explosive.

FIG. 6 Table 1 The physical data of the NEG layers for 1 MeV upper neutron energy and for 50 mm critical thickness.

FIG. 7 Table 2 The Candidate Nuclear Reactions For The CW and HE Identification.

FIG. 8 Table 3 List of elemental Composition, in Weight %, of CW Agents and High Explosive.

FIG. 9 Table 4 List of key Chemical Elements For CW and HE Identification.

FIG. 10 Table 5 List of thermal Neutron Reactions: 0.025 eV-0.5 eV.

FIG. 11 Table 6 List of resonance Neutron Reactions: 0.5 eV-10 keV.

FIG. 12 Table 7 List of threshold Neutron Reactions: 10 keV-20 MeV.

SUMMARY OF THE INVENTION

One embodiment of the present invention is the unique structure of the neutrons generator that included a free-energy ionization method based on electrochemical principal. The neutrons generator comprises the following elements as indicated by their numbers in FIG. 3: a vacuum chamber (1) with grounding connection (11) with exit opening (8), an element (2) of feeding the gaseous fusion fuel (deuterium or deuterium+tritium), an element (3) of ionizing the fusion fuel (deuterium or deuterium+tritium) with electrochemical apparatus porous or mesh that has greater standard electrode reduction-potential than hydrogen and its isotopes (chosen platinum), an element (4) of separating the positive and negative ions with dc voltage supplied by an external high-current power supply (14), an element (5) isolating the electric connections from the chamber made of ceramic, an element (6) of focusing the ion beam with permanent magnet, an element (7) of accelerating the positive fusion beam via cylindrical grid biased by an external high-voltage dc power supply (13), an element (9) of thermalizing the fast neutrons with neutron energy grating NEG hemispheric configuration, an element (10) of reflecting the neutrons around the exit part of the emitted neutrons.

Second embodiment is the capacitative operation of the neutron generator in a sub-breakdown regime as explained in FIG. 2.

Third embodiment includes the analysis of identifying the explosives and chemical warfare.

DETAILED DESCRIPTION OF THE INVENTION

I-1) The Concept of Neutrons Activation

The main steps involved in neutron detection of explosives are shown in FIG. 1. The first step is to irradiate the target to thermal, epithermal, and fast neutrons generated from a special neutron source for a length of time. Consequently, primary and secondary gamma radiation "γ" are generated in all directions. The primary γ results from thermal and epithermal neutron reactions, whereas the secondary γ results from threshold reactions. By placing HPGe (High-Purity-Germanium) coaxial detectors at different locations linked to MCA (Multi Channel Analyzer), the elements can be identified according to the energy of gamma radiations.

1-2) The Neutrons Generator

The present invention is a neutron generator designed to operate in a sub-breakdown regime. It refers to a steady state fusion capacitative device. The operation of the fusion device in sub-breakdown regime yields to higher neutron production efficiency than after the breakdown as shown in FIG. 2. The main components of the neutron generator are shown in FIG. 3. It is composed of a vacuum cylinder (1). The inner components of the vacuum cylinder are the deuterium feed-through (2), platinum mesh or grid (3), dc rings (4), accelerating grid (7), neutron energy grating NEG thermalizer (9), and neutron reflector (10). The outer components are the vacuum pump (not shown in the Figure), permanent magnet (6), high-current dc power supply (14), and high-voltage dc power supply (13).

The objective of the platinum grid is to ionize the deuterium gas $D_2$ through the following electrochemical reaction

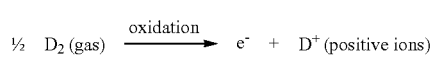

$$\tfrac{1}{2}\ D_2\ (gas) \xrightarrow{oxidation} e^- + D^+ (positive\ ions) \qquad 1$$

According to the standard electrode potential, the reduction energy for platinum is 1.2 V and for hydrogen (isotope of deuterium) is 0.0 V. According to electrochemistry platinum is reduced and hydrogen $H_2$ is oxidized as shown, in reaction 1 for deuterium. In addition platinum is not reactive with hydrogen.

The deuterium positive ions and electrons are segregated by applying a dc voltage on coaxial rings. The electrons are guided by the outer positive ring and deuterium $D_2$ positive ions are guided by the inner negative ring. The applied dc voltage in this region is up to 40 V, but it could be less or more.

The $D_2$ ion beam will be then focused by a magnetic field initiated by a permanent magnet placed at the outside of the vacuum chamber. The deuterium ion beam is then accelerated by a negative voltage 50-80 kV applied to a cylindrical grid while the chamber wall is grounded (positive with respect to the grid). A neutron reflector is placed around the upper part of the vacuum cylinder to stop the neutrons from being travel in any direction but the axial one. The neutron reflector is any material that is able to backscatter the neutrons such as graphite. The fusion reaction D-D is taking place inside the cylindrical grid according to reactions 2 and 3.

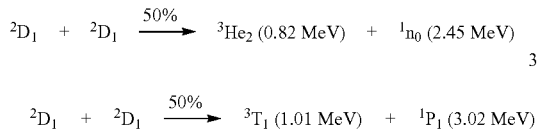

$$^2D_1 + {}^2D_1 \xrightarrow{50\%} {}^3He_2 \,(0.82 \text{ MeV}) + {}^1n_0 \,(2.45 \text{ MeV}) \qquad 2$$

$$^2D_1 + {}^2D_1 \xrightarrow{50\%} {}^3T_1 \,(1.01 \text{ MeV}) + {}^1P_1 \,(3.02 \text{ MeV}) \qquad 3$$

Reactions 2 and 3 are initiated below the normal (Paschen curve) breakdown region (voltage×pressure/diameter) which is equal to (4 kV×mTorr/cm).

The generated fast neutrons (2.45 MeV) from Equation 2 will be then subject to energy reduction by placing a neutron energy grating thermalizer made of polyethylene.

I-3) The NEG Thermalizer

Thermalization (moderation) of neutron occurs if the neutrons lose their energies through elastic and inelastic collisions with present medium. The moderator must be chosen, so that, the absorption of neutrons is insignificant. Two main mechanisms are involved in neutron's moderation; elastic, and inelastic collisions. For the elastic collision, the kinetic energy (in the center of mass system) of the colliding particles is conserved before and after collision. The neutrons transfer a fraction or all of their kinetic energy to the target atoms. For this to happen, the neutrons and the target atoms should have comparable velocities or the distance of separation between target atoms is large enough to allow the motion of targets after the collision. The distance of separation depends on the state of matter, which is lesser in the gaseous state. In the elastic collision, the lighter is the mass, the faster is the energy loss, and the lesser is the material thickness to moderate the neutrons according to the conservation of momentum. For hydrogen moderator, the neutron can lose all of its initial energy in one head-on collision with hydrogen atom (mass=1 amu). In the average, the neutron loses ~50% of its initial energy with hydrogen atom. If comparison is made with heavier atoms, e.g. carbon of mass=12 amu, the neutron can lose in an average 14% of its initial energy by carbon atom. In neutrons activations, it is desirable to obtain neutrons spectrum covers a wide range of neutrons energies. Hence the moderator must be configured to reach to desired objective.

The thermalizer (moderator) is made of polyethylene (similar composition of water) with hemispheric configuration. The neutron energy grating NEG moderator refers to the configuration of the moderator. That is, the thickness of the Polyethylene varies with neutron energy (FIG. 4).

Neutrons moderation is governed by $$E = E_0 e^{-\psi/\tau}. \qquad 4$$

Where: E and $E_0$ are the final and initial neutron energies respectively, $\psi$ is the moderator thickness, $\tau$ is the neutron mean free path respectively. The neutron mean free path, is the distance measured from the point when the neutron is fast (~MeV) to the point when the neutron is slow (~eV). For water, this distance is around 5 cm, and it will be adopted here for Polyethylene.

Equation 4 can be arranged as follows $$\omega_n = \tau \ln(E_0/E_n). \qquad 5$$

Here, we keep $\tau$ as a constant and vary the neutron energy $E_n$. So that, the multiplication of the two factors in the right hand side of Equation 5 gives the moderator thickness at the desired neutron final energy. For the second layer the thickness $t_{n-1}$ is $$\psi_{n-1} = \tau \ln(E_0/E_{n-1}). \qquad 6$$

From Equations 5 and 6, the thickness of the moderator at desired energy is given by $$\psi_{n-1} = \psi_n (\ln(E_0/E_{n-1}))/(\ln(E_0/E_n)). \qquad 7$$

The design of the NEG thermalizer is limited to 1 MeV as an upper limit. This is because the flux should be kept high in the intermediate neutron region. Table 1 summarizes the results of Equation 7.

II) Chemical Warfare Agent and High Explosive Identification

The application of neutrons to identify chemical warfare (CW) agents and high explosive (HE) munitions is the most accurate method and technique. This assay takes place on field without disassembling (non-destructive assay) the agent or the artillery projectiles. The detection and identification of CW agents and HE with neutrons technique can be performed with high level of precession in a short period of time (counting time). Both CW agents and HE used in munitions are organic chemicals rich in carbon, hydrogen, and oxygen.

Each CW agent contains one or more of the elements chlorine, fluorine, sulfur and phosphorus in unique combinations. The neutron assay method is sensitive to the presence of individual chemical elements since the nuclear reactions (absorption and inelastic) take place with each single isotope present in the chemical compound. The artillery projectiles (AP) and the storage containers (SC) will be exposed to thermal, epithermal and fast neutrons from the neutrons generator. The neutrons therefor attenuate (i.e. transmission with collision) the thick steel casing the AP and the SC. Once the neutrons reach to the explosive materials they will undergo elastic, absorption, and inelastic collisions with the present elements (isotopes) in the chemical compounds. The emitted gamma rays (energy range keV-MeV) result from the nuclear reactions will manage to escape the container and provide identification of the chemical elements inside.

For precise identifications, several intermediate and energetic gammas will be detected for each nuclear reaction. Therefore the elemental signature will be based on choosing several isotopes (naturally exist in the element) of which they have high probability of undergoing nuclear reaction (inelastic and absorption). Table 2 lists the candidate nuclear reactions for identifications the CW and HE. These are typical elements that can be found in any explosive materials (standard and nonstandard). The detection time may last few seconds for brief identifications, and few minutes for detailed identifications. The observed gamma ray intensity in the multichannel analyzer MCA indicates precisely to the elements signatures.

For standard explosives the concentrations of contained elements are not necessary. Selected standard explosives are shown in Table 3. Other CW and HE munitions are shown in Table 4.

For stochastic explosives, the concentrations of elements will be determined according to Equation 13. Those explosives contain the major components of explosions but not in standard concentrations. The identifications of the standard and stochastic explosives are the same as illustrated before.

III) Evaluation of Elements Concentrations

The elements concentrations can be determined if we calculate the real reaction rate R in units of transformations per sec. The term "real reaction rate" is defined, here, as the actual number of isotopes that are converted through nuclear reaction per sec and should be observed in the ideal conditions, independent of the sample geometry, detector efficiency, and encountered reactions.

The observed (laboratory) reaction rate $R_L$ can be written as follows $$R_L = R\gamma\eta(1-e^{-\lambda t_r})(1-e^{-\lambda T_c})(1-e^{-\mu\delta}), \quad 8$$

$$R_L = C\lambda e^{\lambda t_d} T_c(\mu\delta). \quad 9$$

Where: $(1-e^{-\lambda t_r})$ is the saturation factor, $t_r$ is the irradiation time, $\lambda$ is the decay constant, $T_c$ is the counting time (live-time), $t_d$ is the decay time, C is the counting rate (net area/$T_c$), $\gamma$ is the gamma emission probability for the product isotope, $\eta$ is the detector efficiency (given by Equation 18), $\delta$ is the thickness of the target in cm, $(1-e^{-\mu\delta})$ is the self-absorption factor, $\mu$ is the mass absorption coefficient (cm$^{-1}$) for particular element. The self-absorption factor is significant for when $\mu\delta>1$ and in this case it can be dropped from Equation From Equations 8 and 9, the real reaction rate R is $$R = (C\lambda e^{\lambda t_d} T_c \mu\delta)/(\gamma\eta(1-e^{-\lambda t_r})(1-e^{-\lambda T_c})(1-e^{-\mu\delta})), \quad 10$$

It might be mentioned that the detector efficiency is implicitly a function of the distance at which the sample will be located from the detector, and of the gamma energy. The detector efficiency will be calibrated against standard source that generate $\gamma$ radiations at different energies. The reaction rate R (in units of reaction per sec) is also written as $$R = N\sigma\phi. \quad 11$$

Where: N is the atomic (isotope) density in units of (# of isotopes/cm$^3$), given by $$N = (0.6023\times10^{24} \text{(atoms/mole)} f(\text{gm/cm}^3)\epsilon(\text{abundance}))/(M \text{ atomic weight (gm/mole)}). \quad 12$$

The mass concentration f is our desired parameter, and to be determined. In equation 12, $\sigma$ is the microscopic absorption cross section (cm$^2$), $\phi$ is the neutron flux at particular neutron energy (#/cm$^2$-sec).

Therefore, the mass concentration f (gm/cm$^3$) of the desired isotope can be found from Equations 10, 11 and 12 which is given by $$f = 1.66\times10^{-24}([C\lambda e^{\lambda t_d} T_c M(\mu\delta)]/[(\gamma\eta(1-e^{-\lambda t_r})(1-e^{-\lambda T_c})(\sigma\phi)_c\epsilon(1-e^{-\mu\delta})]). \quad 13$$

The mass concentration f can be found once the source strength rate $(\sigma\phi)_c$ is calculated at particular neutron energy. Hence, the neutron source must be calibrated against known elements (isotopes) as shown in section III-2.

III-1 Evaluation of the Neutron Flux

As shown in FIG. 5, the portion of the neutron that intercepts the target depends on the geometric factor $\Omega$. The neutron flux $\phi\#$ of neutrons/(cm$^2$-sec) at distance R away from the neutron source $\phi_0$ (# of neutrons/sec) is given by $$\Omega r^2 \phi = \phi_0. \quad 14$$

If the distance of travel R is less than the mean free path 1/$\Sigma$ ($\Sigma$ is the total macroscopic cross section), i.e. for when R$\Sigma$<1, then $\phi$ is given by $$\phi = (\phi_0)/(\Omega r^2). \quad 15$$

Where: $\Omega$ is fraction of neutrons intersected at the target which is equal to H/h, hence Equation 14 becomes $$\phi = (h\phi_0)/(Hr^2). \quad 16$$

III-2) Calibration of the Neutrons Generator

The objective calibrating the neutrons generator is to identify the energy spectrum of the emitted neutrons precisely. The selected elements are those elements which undergo nuclear reactions in the neutron energy range thermal, epithermal and fast energy. Thermal absorption and epithermal (resonance) absorption activation yield to (n,$\gamma$) reactions. Fast activation (threshold) on the other hand, must eject some nuclear particles such as: (n,p), (n,2n), and (n, $\alpha$), eventually the product nuclides will disintegrate through gamma emissions.

Two important parameters should be treated carefully during $(\sigma\phi)_c$ measurements; neutron energy and gamma energy, both must fulfill the following conditions. The first condition is that, the nuclear reaction must be chosen so that it does not occur at more than one neutron energy. If this is not the case, therefore one of them has to have a higher absorption cross section in order to be selected. The second condition is that, the energy of the emitted gamma from one nuclear reaction must not be the same for another nuclear reaction. If this is not the case, then selection of reactions will be based on the natural characteristics; isotopic abundance, gamma emission probability, and half lifetime. The nuclear reaction that has greater natural characteristics will be most likely chosen.

The nuclear reaction Au$^{197}$ (n, $\gamma$) Au$^{198}$ occurs at thermal neutron energy (0.025 eV) and at epithermal neutron energy (4.9 eV), both generate gamma radiations at energies 411.8 keV and 676 keV. The former has an absorption cross section 100 barns whereas the later has 1565 barns (1 barn=10$^{-24}$ cm$^2$). Thus, according to the first condition, the counting rate under those energy peaks represents the epithermal nuclear reaction only. Both above conditions will be considered during on-field investigations.

Tables 5, 6, and 7 list the candidate nuclear reactions for $(\sigma\phi)_c$ measurements. Gamma radiations of high emission relative probabilities (>50%) are considered in these tables. Therefore one can establish a calibration curve that gives $(\sigma\phi)_c$ vs. neutron energy; Equation 17

$$(\sigma\phi)_c = 1.66\times10^{-24}([C\lambda e^{\lambda t_d} T_c M(\mu\delta)]/[(\gamma\eta(1-e^{-\lambda t_r})(1-e^{-\lambda T_c})f\epsilon(1-e^{-\mu\delta})]). \quad 17$$

Equation 17 is an implicitly function of neutron energy. The net count C is the number of counts per second for a particular gamma resonance. This gamma resonance corresponds to neutron energy.

III-3) Calibration of the Gamma Detector

In order to perform neutron activation analysis, the first condition to be met is that the element of interest can undergo a nuclear reaction and exhibit a radioactive isotope of adequate properties. Therefore the probability of the reaction (cross section), the isotope abundance of the target nucleus, and the half-life of the formed isotope should be large enough to allow measurement of the emitted gamma radiation. Type radiation and its energy are also of interest, mainly in overcoming nuclear interferences induced by other impurities.

Gamma detection is usually performed with high purity germanium semiconductor. It is coupled to a multichannel analyzer to facilitate measuring individual gamma energies. The gamma detector must be calibrated to identify the elements of explosives and their concentrations before performing the on-field investigations. It must be calibrated using a reference source of gamma radiations.

The detector efficiency η(E) can be as follows:

$$\eta(E) = (C' e^{\lambda t_d})/(\gamma A). \quad 18$$

Where: C' is the counting rate (net area under peak/live time), λ is the decay constant, $t_d$ is the decay time from the time of standardization to the time of counting, γ is gamma emission probability, A is the activity at the time of standardization.

TABLE 2

| nuclear reaction | energy of emitted γ, keV | γ emission probability (%) | half-life of product isotope | natural abundance of reactant isotope |
|---|---|---|---|---|
| $Al^{27}(n,p)Mg^{27}$ | 843, 1014 | 71.8, 28.2 | 9.45 m | 100 |
| $Al^{27}(n,\alpha)Na^{24}$ | 1368 | 100 | 15 h | 100 |
| $Fe^{58}(n,\gamma)Fe^{59}$ | 1098.6, 1291.5 | 54, 43 | 45 d | 0.31 |
| $Fe^{54}(n,p)Mn^{54}$ | 834.8 | 100 | 291 d | 5.84 |
| $Fe^{56}(n,p)Mn^{56}$ | 846, 1811 | 78.4, 21.6 | 2.58 h | 91.68 |
| $Si^{30}(n,\gamma)Si^{31}$ | 1266.2 | 100 | 2.62 h | 3.05 |
| $Si^{29}(n,p)Al^{29}$ | 1273.3 | 93 | 6.6 m | 4.98 |
| $S^{36}(n,\gamma)S^{37}$ | 3102.4 | 100 | 5 m | 0.017 |
| $S^{34}(n,\alpha)Si^{31}$ | 1266.2 | 100 | 2.62 h | 4.2 |
| $Ge^{76}(n,\gamma)Ge^{77}$ | 211, 215 | 27.2, 27.2 | 11.3 h | 7.67 |
| $Ge^{76}(n,\gamma)Ge^{77m}$ | 215 | 27.2 | 54 s | 7.67 |
| $Ge^{74}(n,\gamma)Ge^{75}$ | 264 | 86 | 82 m | 36.7 |
| $Ge^{74}(n,\gamma)Ge^{75m}$ | 139.8 | 100 | 49 s | 36.7 |
| $P^{31}(n,p)Si^{31}$ | 1266 | 100 | 2.62 h | 100 |
| $F^{19}(n,\gamma)F^{20}$ | 1633 | 100 | 11 s | 100 |
| $As^{75}(n,\gamma)As^{76}$ | 559 | 80.6 | 26.5 h | 100 |
| $Ca^{46}(n,\gamma)Ca^{47}$ | 159.8, 1296.9 | 50.5, 45.4 | 3.43 d, 4.5 d | 0.0033 |
| $Ca^{48}(n,\gamma)Ca^{49}$ | 3084 | 90.9 | 8.72 m | 0.185 |
| $Cl^{37}(n,\gamma)Cl^{38}$ | 1642, 2166 | 58.8, 41.2 | 37.2 m | 24.6 |
| $B^{10}(n,\gamma)B^{11}$ | 477.7 | 100 | n.a** | 80 |
| $O^{18}(n,\gamma)O^{19}$ | 197 | 100 | 29 s | 0.204 |
| $N^{15}(n,\gamma)N^{16}$ | 6129, 7115 | 50, 50 | 7.13 s | 0.37 |
| $H^{1}(n,\gamma)H^{2}$ | 2223.3 | 100 | n.a** | 99.985 |
| $C^{12}(n,p)N^{12}$ | 4439 | 100 | 0.011 s | 98.9 |

*s stands for seconds, m for minutes, h for hours and d for days.
**not available.

TABLE 3

| | CW* and HE** Munitions | | | | |
|---|---|---|---|---|---|
| Element | TNT | Sarin (GB) | (VX) | Mustard (HD) | Lewisite |
| H | 2.2 | 7.1 | 9.7 | 5.0 | 1.0 |
| C | 37.0 | 34.3 | 49.4 | 30.2 | 11.4 |
| O | 42.3 | 22.9 | 12.0 | xxxxx | xxxxx |
| N | 18.5 | xxxxx | 5.2 | xxxxx | xxxxx |
| F | xxxxx | 13.6 | xxxxx | xxxxx | xxxxx |
| Al | xxxxx | xxxxx | xxxxx | xxxxx | xxxxx |
| P | xxxxx | 22.1 | 11.6 | xxxxx | xxxxx |
| S | xxxxx | xxxxx | 12.0 | 20.1 | xxxxx |
| Cl | xxxxx | xxxxx | xxxxx | 44.7 | 51.3 |
| As | xxxxx | xxxxx | xxxxx | xxxxx | 36.1 |

*S. Budavari, ed., The Merck Index, Eleventh Edition Rathaway, N.J: Merck & Inc., 1989.
**R. Meyer, Explosives, Third Edition, New York: VCH Publishers, 1987.

TABLE 4

| Target (Fill) | Containers | Key Elements Secondary Elements |
|---|---|---|
| HD | ton container | Cl, S / C, H |
| VX | land mines | P, S / O, N |
| VX | 155 mm shell | P, S / O, N |
| GB | weteye bomb | P, F / O |
| GB | ton container | P, F / O |
| GB | 155 mm shell | P, F / O |
| TNT | 8 inch shell | Free of: P, F, S and Cl / H, C, O, N |
| Comp. B | 155 mm shell | Free of: P, F, S and Cl / H, C, O, N |

TABLE 5

| neutron energy, eV | nuclear reaction | energy of emitted γ, keV | γ emission probability (%) | $(\sigma \phi)_c$ reactions/sec |
|---|---|---|---|---|
| 0.025 | $Lu^{175}(n,\gamma)Lu^{176m}$ | 88.3 | 100 | to be measured |
| 0.142 | $Lu^{176}(n,\gamma)Lu^{177}$ | 208.4 | 18 | — |

TABLE 6

| neutron energy, eV | nuclear reaction | energy of emitted γ, keV | γ emission probability (%) | $(\sigma \phi)_c$ reactions/sec |
|---|---|---|---|---|
| 1.457 | $In^{115}(n,\gamma)In^{116m}$ | 1293.4, 1097.1 | 38.3, 26.8 | to be measured |
| 4.9 | $Au^{197}(n,\gamma)Au^{198}$ | 411.8 | 100 | — |
| 5.20 | $Ag^{109}(n,\gamma)Ag^{110m}$ | 657.8, 884.5 | 34.4, 25.4 | — |
| 6.7 | $U^{238}(n,\gamma)U^{239}$ | 74.7 | 100 | — |
| 18.8 | $W^{186}(n,\gamma)W^{187}$ | 685.7, 479.3 | 31.4, 26.7 | — |
| 24 | $Th^{232}(n,\gamma)Th^{233}$ | 86.6, 162.3, 169.3, 459.2, 491.1, 499.4, 670.0 | 14 (in all) | — |
| 132 | $Co^{59}(n,\gamma)Co^{60}$ | 1173.1, 1332.4 | 50, 50 | — |
| 230 | $Fe^{58}(n,\gamma)Fe^{59}$ | 1098.6, 1291.5 | 54, 43 | — |
| 337 | $Mn^{56}(n,\gamma)Mn^{57}$ * | 846.9 | 71 | — |
| 480 | $Mo^{98}(n,\gamma)Mo^{99}$ | 140.6 | 74 | — |
| 580 | $Cu^{63}(n,\gamma)Cu^{64}$ ** | 1345.5 | 100 | — |
| 1710 | $Na^{23}(n,\gamma)Na^{24}$ *** | 2753.6, 1368.4 | 52, 48 | — |
| 5000 | $Sc^{45}(n,\gamma)Sc^{46}$ **** | 889.4, 1120.3 | 50, 50 | — |

* Also this reaction occurs at thermal energy (0.025 eV). There is no significant difference for the thermal and resonance neutron energy reactions. The microscopic absorption cross section is 13.2 barns and 14 barns for the thermal and the resonance neutron energy respectively.
** Similarly, the microscopic absorption cross section is 4.5 barns and 5.6 barns for the thermal and resonance neutron energy respectively.
*** The microscopic absorption cross section is 0.54 barns and 0.35 barns for the thermal and resonance neutron energy respectively.
**** The microscopic absorption cross section is 26.5 barns and 11.3 barns for the thermal and resonance neutron energy respectively.

TABLE 7

| neutron energy, MeV | nuclear reaction | energy of emitted γ, keV | γ emission probability (%) | $(\sigma \phi)_c$ reactions/sec |
|---|---|---|---|---|
| 0.1 | $Nb^{93}(n,2n)Nb^{92m}$ | 934.6 | 100 | to be measured |
| 0.8 | $Rh^{103}(n,2n)Rh^{102m}$ | 475.1 | 75.2 | — |
| 1.2 | $In^{115}(n,n')In^{115m}$ | 335 | 46.7 | — |
| 2.2 | $Ti^{47}(n,p)Sc^{47}$ | 159.8 | 100 | — |
| 2.8 | $Zn^{64}(n,p)Cu^{64}$* | 184.2, 93.2 | 58.8, 41.2 | — |
| 2.8 | $Ni^{58}(n,p)Co^{58}$** | 810.3 | 98.8 | — |
| 3.1 | $Fe^{54}(n,p)Mn^{54}$ | 834.8 | 100 | — |
| 3.9 | $Ti^{46}(n,p)Sc^{46}$ | 888, 1119 | 50, 50 | — |
| 4.4 | $Al^{27}(n,p)Mg^{27}$ | 843, 1014 | 71.8, 28.2 | — |
| 6.0 | $Fe^{56}(n,p)Mn^{56}$ | 846, 1811 | 78.4, 21.6 | — |
| 7.2 | $Al^{27}(n,\alpha)Na^{24}$ | 1368 | 100 | — |
| 7.6 | $Ti^{48}(n,p)Sc^{48}$ | 982, 1037, 1311 | 33.6, 32.7, 33.6 | — |

TABLE 7-continued

| neutron energy, MeV | nuclear reaction | energy of emitted γ, keV | γ emission probability (%) | $(\sigma\phi)_c$ reactions/sec |
|---|---|---|---|---|
| 11.0 | $Nb^{93}(n,2n)Nb^{92m}$ | 934.6 | 100 | — |
| 11.5 | $V^{51}(n,\alpha)Sc^{48}$ | 983.5, 1037.4 | 50.5, 49.5 | — |
| 13.5 | $Ni^{58}(n,2n)Ni^{57}$ | 1378.4 | 86.2 | — |

*The microscopic absorption cross section is 30 barns.
**The microscopic absorption cross section is 109 barns.

What is claimed is:

1. An apparatus, comprising: neutrons generator operating in a sub-breakdown (voltage-pressure) regime with free-energy electrochemical ionization element; the neutrons generator including a vacuum chamber linked to a mechanical or turbo pump, an element of feeding the gaseous fusion fuel (deuterium or deuterium+tritium), an element of electrochemical ionizing the fusion fuel (deuterium or deuterium+tritium) with electrochemical apparatus porous or mesh that has greater standard electrode reduction-potential than hydrogen and its isotopes (chosen platinum), an element of separating the positive and negative ions with dc voltage supplied by an external high-current power supply, an element of focusing the ion beam with permanent magnet, an element of accelerating the positive fusion beam via cylindrical grid biased by an external high-voltage dc power supply, an element of thermalizing the fast neutrons with neutron energy grating NEG hemispheric configuration, an element of reflecting the neutrons around the exit part of the emitted neutrons.

2. The apparatus of claim 1, operating in a sub-breakdown (voltage-pressure) regime with free-energy electrochemical ionization element, further comprising an element of accelerating the positive fusion beam via a grid of any configuration.

3. The apparatus of claims 1 or 2, further comprising the uses of neutrons generator in detecting stationary and/or moveable explosives and chemical warfare carried by any means.

* * * * *